US011266772B2

(12) United States Patent
McCrea et al.

(10) Patent No.: US 11,266,772 B2
(45) Date of Patent: Mar. 8, 2022

(54) USE OF HEPARIN AND CARBOHYDRATES TO TREAT CANCER

(71) Applicant: EXTHERA MEDICAL CORPORATION, Berkeley, CA (US)

(72) Inventors: Keith McCrea, Concord, CA (US); Robert Ward, Orinda, CA (US); Olle Larm, Bromma (SE)

(73) Assignee: ExThera Medical Corporation, Martinez, CA (US)

( * ) Notice: Subject to any disclaimer, the term of this patent is extended or adjusted under 35 U.S.C. 154(b) by 0 days.

(21) Appl. No.: 14/565,387

(22) Filed: Dec. 9, 2014

(65) Prior Publication Data

US 2015/0111849 A1    Apr. 23, 2015

Related U.S. Application Data

(63) Continuation of application No. PCT/US2013/042377, filed on May 23, 2013.

(60) Provisional application No. 61/659,337, filed on Jun. 13, 2012.

(51) Int. Cl.
| | | |
|---|---|---|
| *A61K 31/727* | (2006.01) | |
| *A61M 1/34* | (2006.01) | |
| *A61M 1/36* | (2006.01) | |

(52) U.S. Cl.
CPC ............. *A61M 1/34* (2013.01); *A61K 31/727* (2013.01); *A61M 1/3679* (2013.01); *A61M 2202/0478* (2013.01); *A61M 2202/07* (2013.01); *A61M 2205/3334* (2013.01); *A61M 2205/7545* (2013.01)

(58) Field of Classification Search
None
See application file for complete search history.

(56) References Cited

U.S. PATENT DOCUMENTS

| | | | |
|---|---|---|---|
| 3,782,382 A | 1/1974 | Naftulin et al. | |
| 4,103,685 A | 8/1978 | Lupien et al. | |
| 4,415,665 A | 11/1983 | Mosbach et al. | |
| 4,430,496 A | 2/1984 | Abbott | |
| 4,613,665 A | 9/1986 | Larm | |
| 4,637,994 A | 1/1987 | Tani et al. | |
| 4,820,302 A | 4/1989 | Woodroof | |
| 4,955,870 A | 9/1990 | Ridderheim et al. | |
| 5,116,962 A | 5/1992 | Stueber et al. | |
| 5,211,850 A | 5/1993 | Shettigar et al. | |
| 5,403,917 A | 4/1995 | Boos et al. | |
| 5,437,861 A | 8/1995 | Okarma et al. | |
| 5,447,859 A | 9/1995 | Prussak | |
| 5,476,509 A | 12/1995 | Keogh, Jr. et al. | |
| 5,753,227 A * | 5/1998 | Strahilevitz | A61M 1/3679 210/638 |
| 6,037,458 A | 3/2000 | Hirai et al. | |
| 6,159,377 A | 12/2000 | Davankov et al. | |
| 6,197,568 B1 | 3/2001 | Marks et al. | |
| 6,248,127 B1 | 6/2001 | Shah et al. | |
| 6,312,907 B1 | 11/2001 | Guo et al. | |
| 6,461,665 B1 | 10/2002 | Scholander | |
| 6,544,727 B1 | 4/2003 | Hei | |
| 6,559,290 B1 | 5/2003 | Nakatani et al. | |
| 6,653,457 B1 | 11/2003 | Larm et al. | |
| 7,179,660 B1 | 2/2007 | Kirakossian | |
| 7,408,045 B2 | 8/2008 | Maruyama et al. | |
| 7,695,609 B2 | 4/2010 | Soundarrajan et al. | |
| 8,663,148 B2 | 3/2014 | Larm et al. | |
| 8,758,286 B2 | 6/2014 | Ward et al. | |
| 9,173,989 B2 | 11/2015 | Larm et al. | |
| 9,408,962 B2 | 8/2016 | Ward et al. | |
| 9,669,150 B2 | 6/2017 | Larm et al. | |
| 9,764,077 B2 | 9/2017 | Larm et al. | |
| 10,086,126 B2 | 10/2018 | Ward et al. | |
| 10,188,783 B2 | 1/2019 | Larm et al. | |
| 10,457,974 B2 | 10/2019 | Ward et al. | |
| 10,487,350 B2 | 11/2019 | Ward et al. | |
| 10,537,280 B2 | 1/2020 | McCrea et al. | |
| 10,639,413 B2 | 5/2020 | McCrea et al. | |

(Continued)

FOREIGN PATENT DOCUMENTS

| | | |
|---|---|---|
| CN | 1395620 A | 2/2003 |
| CN | 101370536 A | 2/2009 |

(Continued)

OTHER PUBLICATIONS

Webb, L., Ehrengruber, M. U., Clark-Lewis, I., Baggiolini, M., & Rot, A. (1993). Binding to heparan sulfate or heparin enhances neutrophil responses to interleukin 8. Proceedings of the National Academy of Sciences, 90(15), 7158-7162. (Year: 1993).*

Waugh, D. J., & Wilson, C. (2008). The interleukin-8 pathway in cancer. Clinical cancer research, 14(21), 6735-6741. (Year: 2008).*

Brat, D. J., Bellaii, A. C., & Van Meir, E. G. (2005). The role of interleukin-8 and its receptors in gliomagenesis and tumoral angiogenesis. Neuro-oncology, 7(2), 122-133. (Year: 2005).*

Andrade-Gordon, P., & Strickland, S. (1986). Interaction of heparin with plasminogen activators and plasminogen: effects on the activation of plasminogen. Biochemistry, 25(14), 4033-4040. (Year: 1986).*

Andreasen, P. A., Egelund, R., & Petersen, H. H. (2000). The plasminogen activation system in tumor growth, invasion, and metastasis. Cellular and Molecular Life Sciences CMLS, 57(1), 25-40. (Year: 2000).*

(Continued)

*Primary Examiner* — Dale R Miller
(74) *Attorney, Agent, or Firm* — Kilpatrick Townsend & Stockton LLP

(57) ABSTRACT

The method is described as the removal of mediators that contribute to the pathogenesis of cancer from blood by contacting the blood with a solid, essentially non-microporous substrate which has been surface treated with heparin, heparan sulfate and, optionally, other molecules or chemical groups (the adsorbent media or media) having a binding affinity to the mediator, and wherein the size of the interstitial channels within said substrate are balanced with the amount of interstitial substrate surface area such that high flow rates of blood past said substrate creates a flow transport that is characterized by convection transport more than Brownian diffusion transport.

6 Claims, No Drawings

(56) References Cited

U.S. PATENT DOCUMENTS

| | | |
|---|---|---|
| 10,688,239 B2 | 6/2020 | Larm et al. |
| 10,786,615 B2 | 9/2020 | Ward et al. |
| 10,857,283 B2 | 12/2020 | Ward et al. |
| 2001/0005487 A1 | 6/2001 | Kamibayashi et al. |
| 2002/0018985 A1 | 2/2002 | Eibl et al. |
| 2002/0040012 A1 | 4/2002 | Stiekema et al. |
| 2002/0058032 A1 | 5/2002 | Hirai et al. |
| 2002/0068183 A1 | 6/2002 | Huang et al. |
| 2002/0197249 A1 | 12/2002 | Brady et al. |
| 2002/0197252 A1 | 12/2002 | Brady et al. |
| 2003/0021780 A1 | 1/2003 | Smith et al. |
| 2003/0044769 A1 | 3/2003 | Ogino et al. |
| 2003/0148017 A1 | 8/2003 | Tuominen et al. |
| 2004/0084358 A1 | 5/2004 | O'Mahony et al. |
| 2004/0115278 A1 | 6/2004 | Putz et al. |
| 2004/0140265 A1 | 7/2004 | Lihme |
| 2004/0176672 A1 | 9/2004 | Silver et al. |
| 2004/0182783 A1 | 9/2004 | Walker et al. |
| 2004/0185553 A9 | 9/2004 | Hei |
| 2004/0202783 A1 | 10/2004 | Baumann et al. |
| 2005/0098500 A1 | 5/2005 | Collins et al. |
| 2005/0142542 A1 | 6/2005 | Hei et al. |
| 2005/0244371 A1 | 11/2005 | Lentz |
| 2005/0271653 A1 | 12/2005 | Strahilevitz |
| 2006/0030027 A1 | 2/2006 | Ellson et al. |
| 2006/0093999 A1 | 5/2006 | Hei |
| 2006/0252054 A1 | 11/2006 | Ping |
| 2007/0190050 A1 | 8/2007 | Davidner et al. |
| 2007/0218514 A1 | 9/2007 | Smith et al. |
| 2007/0231217 A1 | 10/2007 | Clinton et al. |
| 2008/0021365 A1 | 1/2008 | Kobayashi et al. |
| 2008/0138434 A1 | 6/2008 | Brady et al. |
| 2008/0268464 A1 | 10/2008 | Schumacher et al. |
| 2008/0314817 A1 | 12/2008 | Fujita et al. |
| 2009/0105194 A1 | 4/2009 | Flengsrud et al. |
| 2009/0136586 A1 | 5/2009 | Larm et al. |
| 2009/0173685 A1 | 7/2009 | Imai et al. |
| 2009/0186065 A1 | 7/2009 | Tillman et al. |
| 2009/0206038 A1 | 8/2009 | Thomas |
| 2009/0246800 A1 | 10/2009 | Mattingly et al. |
| 2009/0325276 A1 | 12/2009 | Battrell |
| 2010/0021622 A1 | 1/2010 | Meng et al. |
| 2010/0040546 A1 | 2/2010 | Hyde et al. |
| 2010/0069816 A1 | 3/2010 | Brady et al. |
| 2010/0079360 A1 | 4/2010 | McLaughlin et al. |
| 2010/0098666 A1 | 4/2010 | Wright |
| 2010/0112725 A1 | 5/2010 | Babu et al. |
| 2010/0145317 A1 | 6/2010 | Laster et al. |
| 2010/0216226 A1 | 8/2010 | Hyde et al. |
| 2010/0217173 A1 | 8/2010 | Hyde et al. |
| 2010/0239673 A1 | 9/2010 | Linhardt |
| 2010/0249689 A1 | 9/2010 | Larm et al. |
| 2010/0276359 A1 | 11/2010 | Ippommatsu et al. |
| 2010/0291588 A1 | 11/2010 | McDevitt |
| 2010/0326916 A1 | 12/2010 | Wrazel et al. |
| 2011/0150911 A1 | 6/2011 | Choo |
| 2011/0171713 A1 | 7/2011 | Bluchel et al. |
| 2011/0184377 A1 | 7/2011 | Ward et al. |
| 2011/0224645 A1 | 9/2011 | Winqvist et al. |
| 2012/0040429 A1 | 2/2012 | Federspiel et al. |
| 2012/0219561 A1* | 8/2012 | Alt .................... C07K 16/18 424/158.1 |
| 2012/0305482 A1 | 12/2012 | McCrea et al. |
| 2013/0102948 A1 | 4/2013 | Reich et al. |
| 2013/0131423 A1 | 5/2013 | Wang et al. |
| 2014/0012097 A1 | 1/2014 | McCrea et al. |
| 2014/0131276 A1 | 5/2014 | Larm et al. |
| 2014/0231357 A1 | 8/2014 | Ward et al. |
| 2015/0260715 A1 | 9/2015 | Hu et al. |
| 2016/0022898 A1 | 1/2016 | Larm et al. |
| 2016/0082177 A1 | 3/2016 | Ward et al. |
| 2016/0084835 A1 | 3/2016 | Ward et al. |
| 2016/0101229 A1 | 4/2016 | McCrea et al. |
| 2016/0214935 A1 | 7/2016 | Hutchinson et al. |
| 2016/0331886 A1 | 11/2016 | Ward et al. |
| 2017/0035956 A1 | 2/2017 | McCrea et al. |
| 2017/0073727 A1 | 3/2017 | Ward et al. |
| 2017/0340803 A1 | 11/2017 | Larm et al. |
| 2018/0361050 A1 | 12/2018 | Ward et al. |
| 2019/0038826 A1 | 2/2019 | McCrea et al. |
| 2019/0143027 A1 | 5/2019 | Larm et al. |
| 2020/0056221 A1 | 2/2020 | Ward et al. |
| 2020/0171233 A1 | 6/2020 | McCrea et al. |
| 2020/0297913 A1 | 9/2020 | Larm et al. |
| 2020/0338256 A1 | 10/2020 | Ward et al. |

FOREIGN PATENT DOCUMENTS

| | | |
|---|---|---|
| CN | 101784294 A | 7/2010 |
| CN | 102740859 A | 10/2012 |
| CN | 102791307 | 11/2012 |
| CN | 106255520 A | 12/2016 |
| DE | 4217917 A1 | 12/1993 |
| EP | 0 306 617 A | 3/1989 |
| EP | 0 321 703 A | 6/1989 |
| EP | 0533946 A1 | 3/1993 |
| EP | 0 616 845 A | 9/1994 |
| EP | 0 810 027 A | 12/1997 |
| EP | 1044696 A2 | 10/2000 |
| EP | 1 057 529 A | 12/2000 |
| EP | 1 110 602 A | 6/2001 |
| EP | 1 219 639 A | 7/2002 |
| EP | 2087916 A1 | 8/2009 |
| EP | 2556849 A1 | 2/2013 |
| GB | 2 172 812 A | 10/1986 |
| JP | 54-127493 U | 9/1979 |
| JP | 58-053757 A | 3/1983 |
| JP | 58-146354 A | 8/1983 |
| JP | 4-89500 A | 3/1992 |
| JP | 6040926 A | 2/1994 |
| JP | 6-505248 A | 6/1994 |
| JP | 7-178161 A | 7/1995 |
| JP | 96-510166 A | 10/1996 |
| JP | 11-502703 A | 3/1999 |
| JP | 2000-086688 A | 3/2000 |
| JP | 2000-217575 A | 8/2000 |
| JP | 2000-515543 A | 11/2000 |
| JP | 2001-190273 A | 7/2001 |
| JP | 2002-505101 A | 2/2002 |
| JP | 2002-509518 A | 3/2002 |
| JP | 2003-128502 A | 5/2003 |
| JP | 2003-520048 A | 7/2003 |
| JP | 2005-514127 A | 5/2005 |
| JP | 2005-519744 A | 7/2005 |
| JP | 2005-532130 A | 10/2005 |
| JP | 2009-521413 A | 6/2009 |
| JP | 2010-518046 A | 5/2010 |
| JP | 2010-530288 A | 9/2010 |
| JP | 2011-509083 A | 3/2011 |
| JP | 2012-501708 A | 1/2012 |
| JP | 2013-512078 A | 4/2013 |
| JP | 2014-500735 A | 1/2014 |
| JP | 2014-523914 A | 9/2014 |
| KR | 10-2008-0077405 A | 8/2008 |
| WO | 91/04086 A | 4/1991 |
| WO | 92/14361 A1 | 9/1992 |
| WO | 94/26399 A1 | 11/1994 |
| WO | 95/05400 | 2/1995 |
| WO | 96/29083 A1 | 9/1996 |
| WO | 96/40857 A1 | 12/1996 |
| WO | 97/35660 A1 | 10/1997 |
| WO | 98/05341 A1 | 2/1998 |
| WO | 98/29727 A2 | 7/1998 |
| WO | 99/06086 A1 | 2/1999 |
| WO | 99/45104 A3 | 11/1999 |
| WO | 00/23792 | 4/2000 |
| WO | 00/038763 | 7/2000 |
| WO | 00/66260 A | 11/2000 |
| WO | 01/18060 A | 3/2001 |
| WO | 01/53525 A2 | 7/2001 |
| WO | 02/060512 | 8/2002 |
| WO | 03/033143 A1 | 4/2003 |
| WO | 2003/057356 A2 | 7/2003 |
| WO | 2003/078023 A1 | 9/2003 |

(56) References Cited

FOREIGN PATENT DOCUMENTS

| WO | 2004/008138 | A2 | 1/2004 | | |
|---|---|---|---|---|---|
| WO | 2004/009798 | A2 | 1/2004 | | |
| WO | 2005/021799 | A2 | 3/2005 | | |
| WO | 2007/058592 | A1 | 5/2007 | | |
| WO | 2007/069983 | A1 | 6/2007 | | |
| WO | 2007/101064 | A2 | 9/2007 | | |
| WO | 2007/146162 | A2 | 12/2007 | | |
| WO | 2008/095905 | A2 | 8/2008 | | |
| WO | 2008/157570 | A2 | 12/2008 | | |
| WO | 2009/086343 | A2 | 7/2009 | | |
| WO | 2010/029317 | A2 | 3/2010 | | |
| WO | 2011/068897 | A1 | 6/2011 | | |
| WO | 2011/100354 | A1 | 8/2011 | | |
| WO | 2012/051595 | A1 | 4/2012 | | |
| WO | 2012/112724 | A1 | 8/2012 | | |
| WO | 2012/172341 | A2 | 12/2012 | | |
| WO | WO-2012172341 | A2 * | 12/2012 | ........... | C07K 14/521 |
| WO | 2013/012924 | A2 | 1/2013 | | |
| WO | 2013/188073 | A1 | 12/2013 | | |
| WO | 2014/209782 | A1 | 12/2014 | | |
| WO | 2015/069942 | A1 | 5/2015 | | |
| WO | 2015/164198 | A1 | 10/2015 | | |

OTHER PUBLICATIONS

Choong, P. F., & Nadesapillai, A. P. (2003). Urokinase plasminogen activator system: a multifunctional role in tumor progression and metastasis. Clinical orthopaedics and related research, (415 Suppl), S46-58. (Year: 2003).*

Smorenburg, S. M., & Van Noorden, C. J. (2001). The complex effects of heparins on cancer progression and metastasis in experimental studies. Pharmacological reviews, 53(1), 93-106. (Year: 2001).*

Murphy, J. W., Cho, Y., Sachpatzidis, A., Fan, C., Hodsdon, M. E., & Lolis, E. (2007). Structural and functional basis of CXCL12 (stromal cell-derived factor-1α) binding to heparin. Journal of Biological Chemistry, 282(13), 10018-10027. (Year: 2007).*

Ok, S., Kim, S. M., Kim, C., Nam, D., Shim, B. S., Kim, S. H., . . . & Ahn, K. S. (2012). Emodin inhibits invasion and migration of prostate and lung cancer cells by downregulating the expression of chemokine receptor CXCR4. Immunopharmacology and immunotoxicology, 34(5), 768-778. (Year: 2012).*

Utt, M. et al., "Identification of heparan sulphate binding surface proteins of Helicobacter pylori inhibition of heparan sulphate binding with sulphated carbohydrate polymers," J. Med. Microbiol., 46:541-546, 1997.

Abdul-Razzak, K. et al., "Fetal and newborn calf thymus as a source of chromatin proteins Purification of HMG-1 and HMG-2," Preparative Biochemistry and Biotechnology, 17(1):51-61, 1987.

Alarabi, A. et al., "Treatment of pruritus in cholestatic jaundice by bilirubin- and bile acid-adsorbing resin column plasma perfusion," Scandinavian Journal of Gastroenterology, 27(3):223-6, 1992.

Chase, H., "Affinity separations utilising immobilised monoclonal antibodies—a new tool for the biochemical engineer," Chemical Engineering Science, 39(7-8): 1099-1125, 1984.

Garg, L. et al., "Isolation and separation of HMG proteins and histones H1 and H5 and core histones by column chromatography on phosphocellulose," Protein Expression and Purification, 14(2): 155-159, 1998.

Low, R. et al., "Protein n, a primosomal DNA replication protein of *Escherichia coli*," Journal of Biological Chemistry, 257(11):6242-6250, 1982.

Rauvala, H. et al., "Isolation and some characteristics of an adhesive factor of brain that enhances neurite outgrowth in central neurons," Journal of Biological Chemistry, 262(34):16625-16635, 1987.

Rauvala, H. et al., "The adhesive and neurite-promoting molecule p30: Analysis of the aminoterminal sequence and production of antipeptide antibodies that detect p30 at the surface of neuroblastoma cells and of brain neurons," Journal of Cell Biology, 107(6,1):2293-2305, 1988.

Salmivirta, M. et al., "Neurite growth-promoting protein (Amphoterin, p30) binds syndecan," Experimental Cell Research, 200:444-451, 1992.

Sato, T. et al., "Experimental study of extracorporeal perfusion for septic shock," Asaio Journal, 39(3):M790-M793, 1993.

Wang, H. et al., "HMG-1 as a late mediator of endotoxin lethality in mice," Science, 285:248-251, 1999.

Bindslev et al., "Treatment of acute respiratory failure by extracorporeal carbon dioxide elimination performed with a surface heparinized artificial lung," Anesthesiology, 67(1):117-120, 1987.

Bjorklund et al., Abstract of "Synthesis of silica-based heparin-affinity adsorbents," J. Chrom. A., 728(1-2):149-169, 1996.

Chen et al., "Microbial subversion of heparin sulfate proteoglycans," Mol. Cells, 26:415-426, 2008.

Dixon et al., "Anthrax," New England Journal of Medicine, 341(11):815-826, 1999.

Dubreuil et al., "Effect of heparin binding on Helicobacter pylori resistance to serum," J. Med. Micro., 53:9-12, 2004.

Fujita, M. et al., "Adsorption of inflammatory cytokines using a heparin-coated extracorporeal circuit," Artificial Organs, 26(12):1020-1025, 2002.

Haase et al., "The effect of three different miniaturized blood purification devices on plasma cytokine concentration in an ex vivo model of endotoxinemia," Int. J. Artif. Organs, 31(8):722-729, 2008.

Hirmo, S. et al., "Sialyglycoconjugate- and proteoglycan-binding microbial lectins," Institute of Medical Microbiology, University of Lund, (Online). Retrieved Oct. 19, 1997 (Retrieved on Mar. 16, 2004). Retrieved from the Internet: <URL: http//www.plab.ku.dk/tcbh/Lectins12/Hirmo/paper.htm>.

International Preliminary Report on Patentability, dated Aug. 21, 2013, PCT Application No. PCT/US2012/025316; 8 pages.

International Search Report; PCT/US2012/025316 dated May 23, 2012.

International Search Report; PCT/US2010/058596 dated Mar. 29, 2011.

International Search Report; PCT/US2011/024229 dated May 30, 2011.

International Search Report; PCT/SE2006/001421 dated Mar. 30, 2007.

International Search Report; PCT/US2013/042377 dated Sep. 9, 2013.

International Search Report; PCT/US2014/043358 dated Dec. 1, 2014.

International Search Report; PCT/US2014/064419 dated Feb. 12, 2015.

Keuren et al., "Thrombogenecity of polysaccharide-coated surfaces," Biomaterials, 24:1917-1924, 2003.

Kim et al., "Role of the heparin in regulating a transcapillary exchange in far north conditions," Bulletin of the Siberian Branch of the Russian Academy of Medical Sciences, 2(108), 2003.

Larm et al., "A new non-thrombogenic surface prepared by selective covalent binding of heparin via a modified reducing terminal residue," Biomater Med Devices Artif Organs, 11 (2&3):161-173, 1983.

Lopatkin et al., "Efferent methods in medicine, M.," Medicine, pp. 266, 272-273, 276-279, 1989.

Mandal, "Sialic acid binding lectins," Experientia, 46:433-439, 1990.

Mariano et al., "Tailoring high-cut-off membranes and feasible application in sepsis-associated acute renal failure: in vitro studies," Nephrol Dial Transplant, 20:1116-1126, 2005.

Montelius et al., Biomaterials, 15:805-814, 1994.

Nadkarni et al., Abstract of "Directional immobilization of heparin onto beaded supports," Anal. Biochem., 222(1):59-67, 1994.

Ofek et al., "Mannose binding and epithelial cell adherence of *Escherichia coli*," Infection and Immunity, 22(1):247-254, 1978.

Park, P. et al., "Activation of Syndecan-1 ectodomain shedding by *Staphylococcus aureus* α-toxin and β-toxin," J. Biol. Chem., 279(1):251-258, 2004.

Popova et al., "Acceleration of epithelial cell syndecan-1 shedding by anthrax hemolytic virulence factors," BMC Microbiolgy, 6:8, pp. 1-16, 2006.

(56) References Cited

OTHER PUBLICATIONS

Riesenfeld et al., "Quantitative analysis of N-sulfated, N-acetylated, and unsubstituted glucosamine amino groups in heparin and related polysaccharides," Anal Biochem, 188:383•389, 1990.

Sagnella et al., "Chitosan based surfactant polymers designed to improve blood compatibility on biomaterials," Colloids and Surfaces B: Biointerfaces, 42:147-155, 2005.

Sanchez, J. et al., "Control of contact activation on end-point immobilized heparin: The role of antithrombin and the specific antithrombin-binding sequence," J. Bio. Mat. Res., 29:665-661, 1995.

Sasaki et al., Abstract of "Improved method for the immobilization of heparin," J. Chrom., 400:123-32, 1987.

Schefold et al., "A novel selective extracorporeal intervention in sepsis: immunoadsorption of endotoxin, interleukin 6, and complement-activating product 5A," Shock, 28(4):418-425, 2007.

Sharon, "Bacterial lectins, cell-cell recognition and infectious disease," FEBS letters, 217(2):145-157, 1987.

Swartz, "Recognition and management of anthrax—an update," New England Journal of Medicine, 345(22):1621-1626, 2001.

Thomas et al., "Common oligosaccharide moieties inhibit the adherence of typical and atypical respiratory pathogens," Journal of Microbiology, 53:833-840, 2004.

Ward et al., "Specificity of adsorption in a prototype whole blood affinity therapy device for removal of *Staphylococcus aureus*," Society for Biomaterials 2013 Annual Meeting and Exposition, Apr. 10, 2013, p. 1.

Weber et al., "Development of specific adsorbents for human tumor necrosis factor-α: influence of antibody immobilization on performance and biocompatibility," Biomacromolecules, 6:1864•1870, 2005.

Weir, D., "Carbohydrates as recognition molecules in infection and immunity," FEMS Microbiology Immunology, 47:331-340, 1989.

Wendel et al., "Coating-techniques to improve the hemocompatibility of artificial devices used for extracorporeal circulation," European Journal of Cardio-thoracic Surgery, 16:342-350, 1999.

Zhou et al., Abstract of "Heparin-agarose aqueous ethanol suspension," J. Mol. Bio., 271 (3):12, 1997.

International Search Report; PCT/US2015/026340 dated Jul. 28, 2015.

International Search Report; PCT/US2015/051239 dated Dec. 17, 2015.

Bhakdi, S. and Tranum-Jensen, J., "Alpha-toxin of *Staphylococcus aureus*," Microbiological Reviews, 55(4):733-751, 1991.

International Search Report; PCT/US2016/057121; dated Dec. 30, 2016.

Celik, T. et al., "Treatment of lyme neuroborreliosis with plasmapheresis," J. Clinical Apheresis, 31:476-478, 2016.

Francy, D. et al., "Comparison of filters for concentrating microbial indicators and pathogens in lake water samples," Applied and Environmental Microbiology, 79(4):1342-52, 2012.

Millen, H. et al., "Glass wool filters for concentrating waterborne viruses and agricultural zoonotic pathogens," J. Vis. Exp., 61:e3930, 2012.

Axelsson, J. et al., "Cytokines in blood from septic patients interact with surface-immobilized heparin," ASAIO Journal, 56:48-51, 2010.

Kenig, M. et al., "Identification of the heparin-binding domain of TNF-alpha and its use for efficient TNF-alpha purification by heparin-Sepharose affinity chromatography," J. Chromatography B, 867:119-125, 2008.

Kishimoto, S. et al., "Human stem cell factor (SCF) is a heparin-binding cytokine," J. Biochem., 145(3)275-278, 2009.

Salek-Ardakani, S. et al., "Heparin and heparan sulfate bind interleukin-10 and modulate its activity," Blood, 96:1879-1888, 2000.

International Search Report; PCT/US2017/058536; dated Jan. 17, 2018.

Alfaro et al., "Interleukin-8 in cancer pathogenesis, treatment and follow-up," Cancer Treat Rev., Nov. 2017, vol. 60:24-31 (abstract only).

Kumari, "Role of interleukin-6 in cancer progression and therapeutic resistance," Tumour Biol., Sep. 2016, vol. 37(9), pp. 11553-11572 (abstract only).

Lian, Shuijin et al., "Elevated expression of growth-regulated oncogene-alpha in tumor and stromal cells predicts unfavorable prognosis in pancreatic cancer," Medicine, Jul. 2016, 95(30)), pp. 1-8.

Mattsby-Baltzer, I. et al., "Affinity apheresis for treatment of bacteremia caused by *Staphylococcus aureus* and/or methicillin-resistant *S. aureus* (MRSA)," J. Microbiol. Biotechnol., 21(6):659-664, 2011.

GE Healthcare, "Size exclusion chromatography cols. and resins, Selection guide," 2010, retreived online at <<https://cdn.gelifesciences.com/dmm3bwsv3/AssetStream.aspx?mediaformatid=10061&destination id=10016&assetid=13947>> on Jun. 27, 2019, 10 pages.

Ghannoum, M. et al., "Extracorporeal treatment for carbamazepine poisoning: Systematic review and recommendations from the EXTRIP workgroup," Clinical Toxicology, 52:993-1004, 2014.

Lemaire, M. et al., "Treatment of paediatric vancomycin intoxication: a case report and review of the literature," NDT Plus, 3:260-264, 2010.

Ascencio, F. et al., "Affinity of the gastric pathogen Heficobacter py/ori for the N-sulphated glycosaminoglycan heparan sulphate," J. Med. Microbiol., 38:240-244, 1993.

Bartlett, A. and P. Park, "Proteoglycans in host-pathogen interactions: molecular mechanisms and therapeutic implications," Expert Rev. Mol. Med., 12(e5):1-33, 2015.

Era, K. et al., "Development of Systems for Passive and Active CAVH," J. Japanese Society for Dialysis Therapy, 19(2):175-181, 1986.

Frick, I. et al., "Interactions between M proteins of *Streptococcus pyogenes* and glycosaminoglycans promote bacterial adhesion to host cells," Eur. J. Biochem., 270(10):2303-11, 2003.

Office Action dated Jun. 23, 2020 in Japanese Patent Application No. 2017-515161, with English translation, retrieved from <https://globaldossier.uspto.gov/#/details/JP/2017515161/A/129021> on Aug. 13, 2020.

Sanaka, T. et al., "Continuous Arteriovenous Hemofiltration," Artificial Organs, 14(5):1822-1830, 1985.

Tonnaer, E. et al., "Involvement of glycosaminoglycans in the attachment of pneumococci to nasopharyngeal epithelial cells," Microbes and Infection, 8:316-322, 2006, available online Sep. 16, 2005.

Wadstrom, T. and A. Ljungh, "Glycosaminoglycan-binding microbial proteins in tissue adhesion and invasion: key events in microbial pathogenicity," J. Med. Microbiol., 48(3):223-233, 1999.

* cited by examiner

USE OF HEPARIN AND CARBOHYDRATES TO TREAT CANCER

CROSS-REFERENCE TO RELATED APPLICATIONS

This application is a continuation of PCT/US2013/042377, filed May 23, 2013, which application claims the benefit of priority of U.S. Provisional Application No. 61/659,337, filed Jun. 13, 2012, the disclosures of which are hereby incorporated by reference in their entities, for all purposes.

FIELD OF THE INVENTION

The present invention is directed to a method for the removal of mediators that contribute to the pathogenesis of cancer from blood by contacting the blood with a solid, essentially non-micro-porous substrate which has been surfaced treated with heparin, heparin sulfate and, optionally, other molecules or chemical groups (the adsorbent media or media) having a binding affinity to the mediator, and wherein the size of the interstitial channels within said substrate are balanced with the amount of interstitial substrate surface area such that high flow rates of blood past said substrate creates a flow transport that is characterized by convection transport more than Brownian diffusion transport. The present invention also provides a method of treating cancer by removing circulating cancer mediators from blood by contacting blood with a solid substrate coated with heparin, heparan sulfate, and/or other carbohydrates and a device for performing the method and treatment. The present invention also provides a method of treating cancer with surgery to remove malignancies while simultaneously contacting blood with the solid substrate coated with heparin, heparan sulfate, and/or other carbohydrates or supplemental adsorbents to safely remove cancer mediators from the blood generated by the surgery, and a device for performing the method and treatment.

BACKGROUND

Cancer is a very complex disease with many circulating mediators that contribute to the pathogenesis or metastases of tumors. Examples of such mediators include, but are not limited to, circulating tumor cells responsible for metastases, circulating growth factors that contribute to angiogenesis of tumors, circulating cytokines that contribute to angiogenesis, circulating heparanases that degrade heparan sulfate segments on endothelial cell walls that can lead to tumor cell invasion, and circulating fibrin or thrombin that leads to venous thromboembolism.

Heparin is a glycosaminoglycan, which is isolated from mammalian tissue. Since its discovery in 1916 by the American scientist McLean, heparin has been recognized for its blood anticoagulant properties and heparin has, for more than 50 years, been used clinically as a blood anticoagulant and antithrombotic agent.

Heparin has a very particular distribution in mammalian tissue. Heparin is present only in the basophilic granules of mast cells. However, today, in addition to its established place in prevention and therapy of thromboembolic disorders, heparin has demonstrated a broad-spectrum of different activities independent of anticoagulation.

Heparin is very similar to heparan sulfate (HS), which is found in syndecans and glypicans of the extracellular matrix (ECM). HS play an important role in cell signaling at the ECM surface and therefore binds to many different chemical species.

A large number of proteins in blood bind, with high affinity, to heparin and HS. Examples are antithrombin (AT), fibronectin, vitronectin, growth factors (e.g. the fibroblast growth factors, the insulin like growth factors etc). Many cytokines and chemokines, such as TNF-, IL-8, and GRO-, also have a high affinity to heparin or HS.

Recently, several retrospective studies on cancer patients have been performed and the findings indicate patients treated with soluble systemic heparin, either unfractionated or fractionated, appear to have improved survivability. Smorenburg et al., Pharmacol. Rev. 53; 93-1005 (2001). Klerk et al., J. Clin. Oncol., v. 23:10, pages 2130-2135 (2005). However, it is unknown what the mechanism of action of heparin is that may decrease mortality in this patient population. One hypothesis is that because many of the mediators responsible for tumor growth and metastases are heparin binding, the systemic heparin may interfere with disease progression. Additionally, studies indicate that systemic heparin may promote deleterious effects.

It has been found that circulating tumor cells contain heparin binding sequences. Studies have been performed that indicate ECM HS segments promote adhesion of tumor cells from circulating blood. Yip et al., Mol Cancer Ther 2006; 5 (9) 2139-2148. Vlodavsky et al., Rambam Maimonides Med. J., January 2011, v.2:1; e0019, pages 1-17. Sasiskharan et al., Nature Reviews, Cancer, 2; 521-528, 525 (2002). This allows cancer metastases throughout the body. Previous research has hypothesized that systemic heparin may bind to circulating tumor cells, thus blocking binding sites that would normally bind to ECM HS segments.

Angiogenesis is the formation of new blood vessels and is required for tumor growth. The formation of the new blood vessels can also facilitate the release of tumor cells into the blood stream. Several growth factors, such as vascular endothelial growth factor (VEGF) and basic fibroblast growth factor (bFGF) are released from cancer cells along with chemokines and cytokines such as IL-8. When growth factors bind to HS, they are stabilized and stored for later release to aid in angiogenesis. It is possible that systemic heparin binds to VEGF and bFGF which reduces their activity. IL-8 is an important cytokine in angiogenesis and is also known to be heparin or HS binding.

Heparanases also are released by cancer cells and degrade ECM HS by hydrolyzing glycosidic linkages. HS degradation then leads to compromised host tissue and could facilitate tumor cell penetration. Vlodavsky et al., Rambam Maimonides Med. J., January 2011, v.2:1; e0019, pages 1-17. Sasiskharan et al., Nature Reviews, Cancer, July 2002, v.2 pages 521-528, 525. Studies have shown that systemic heparin can inhibit heparanase activity and prevent the degradation of ECM HS segments. Vlodavsky et al., page 9, col. 1.

Systemic heparin may also cause proteolysis and ECM degradation by activating proteolytic enzymes. It has been shown that systemic heparin can locally stimulate pro-uPA (pro-urinary plasminogen activator protein) and plasminogen at the cell surface. The activated pro-uPA and plasminogen can then enhance invasion of human melanoma cells. Elevated uPA levels are correlated with poor prognosis in cancer patients.

Thrombin formation is implicated in cancer cell survival. Thrombin formation promotes adhesion of cancer cells to the endothelium by stimulating II 3 expression on cancer cells. Thrombin also promotes cancer cell and platelet aggregation which can lead to thrombus formation. The thrombin formation can then block the microvasculature in which the cancer cell resides which then protects the cancer cell from mechanical stress and the natural immune response. Systemic heparin inactivates thrombin and may help prevent metastases.

Systemic heparin can either benefit, or potentially harm cancer patients through multiple modes of action. As described above, many of these mediators are heparin binding. Many of the mediators involved in cancer progression can be found in the circulating blood and can affect angiogenesis and metastases. Potential side effects of systemic heparin are increased bleeding risk or heparin induced thrombocytopenia. A potential method to treat cancer patients is to remove these circulating mediators by capturing them on a high surface area adsorbent media modified with heparin. Instead of binding to ECM HS segments within the body, these mediators are bound to the heparin-modified surface of the affinity filtration cartridge and removed from circulation. In addition, risks such as bleeding, heparin-induced thrombocytopenia, and activation of pro-uPA and plasminogen are mitigated because the heparin is not released into the blood stream.

SUMMARY OF THE INVENTION

An object of the present invention is to provide a method for the removal of cancer mediators that contribute to tumor angiogenesis or metastases from mammalian blood by contacting blood with a solid substrate coated with heparin and/or other carbohydrates.

Another object of the invention is to provide a method of treating cancer progression by removing cancer mediators from mammalian blood by contacting mammalian blood with a solid substrate coated with heparin and/or other carbohydrates.

Another object of the invention is to provide an adjunct to cancer surgery by removing cancer mediators from mammalian blood that are generated by the cancer surgery, and which could otherwise cause metastasis of the cancer being treated by the surgery.

The above mentioned objects are not intended to limit the scope of the invention in any way.

A first aspect of the present invention provides a method for the removal of circulating cancer mediators from blood, such as mammalian blood, by contacting the blood with a solid substrate e.g., coated with heparin.

In this method, heparin is immobilized onto the surface of the substrate. Heparin is known to bind many cancer mediators and heparin bound to a surface can be effective for removing a significant amount of mediators from blood. However, the flow rates typical of extracorporeal blood circuits require that the adsorbent 'bed' be designed to allow relatively high flow rates to operate safely. This is in part due to the universal tendency of slow-moving or stagnant blood to form dangerous clots. In the present invention the substrate is designed with sufficiently large interstitial dimensions to permit a high flow rate of blood over the substrate without a large pressure drop. That is, as blood is taken from a mammalian patient, it is passed over the substrate at a flow rate whereby the delivery of adsorbates to the surface of the adsorbent bed is characterized primarily by forced convection. This is in contrast to the much slower process of molecular diffusion that occurs in the use of highly porous adsorbent media (e.g. porous silica, sephadex, crosslinked polystyrene and other size exclusion media), and many other microporous media. Molecular diffusion is also required when selectively-permeable barrier membranes are used together with adsorption media, e.g., to prevent contact of the adsorption media by blood cells and/or high molecular weight solutes during affinity therapy.

The binding of cancer mediators by heparin during convection transport is particularly effective under the relatively high-flow conditions typically employed in the (safe) operation of extracorporeal blood circuits, e.g. when measured by linear flow velocity, ≥8 cm/min, preferably about ≥24 cm/min, and more preferably about 24-329 cm/minute, or, when measured by flow rate, around >50 mL/minute and preferably >150 mL/minute but less than about 2000 mL/minute. Adsorption within the pores of microporous media, in contrast, may require much lower flow rates through adsorption beds of practical size in order to achieve an adequate separation or purification, i.e. <50 mL/min to as low as <1 mL/min.

It is recognized that, strictly speaking, it is 'residence time' on the adsorption column that needs to be much longer for a media requiring diffusive transport of adsorbates to the adsorbent site within the media, when compared to the lower residence time needed to convey an adsorbate to the binding site (on an essentially nonporous media) by forced convection. However, there are practical limits to the dimensions of a safe and effective adsorbent cartridge, column, filter, etc., especially with respect to the maximum hold-up volume of blood it can contain, and the flow velocity of blood or serum past the adsorption media. For this reason average flow rate through the adsorption device is considered to be an important design variable.

Convection kinetics and diffusion kinetics can be compared in the removal of cancer mediators from flowing blood: Adsorption media that depend on diffusion transport generally use very porous materials with extremely high internal surface area due to the presence of microscopic pores. Media suited for convection transport, on the other hand, generally rely on macroscopic "channels" or visible interstices between solid, essential nonporous material, such as particles, beads, fibers, reticulated foams, or optionally spiral-wound dense membranes.

Media that rely on forced convection transport are generally more suitable for high-flow rates, while media that rely on the much slower diffusion transport are much less effective when high flow rates and shorter residence times are required. For this reason, in an extracorporeal blood purification device, an adsorption media that does not require the adsorbate to slowly diffuse into pores within the adsorbent media is much preferred. When blood is pumped through circuits fabricated from man-made materials it is a general practice to employ relatively high blood flow rates in order to prevent stagnation and reduce the risk of clotting. On the other hand, extremely high flow rates must be avoided because they can expose blood cells to high shear rates and impingement damage that can rupture or otherwise damage blood cells. The present invention, therefore, provides a method and device for removing cancer mediators from blood using the preferred characteristics of convection transport and its desirable, more-rapid kinetics. This is achieved by passing/flowing blood over an essentially non-microporous substrate that has been surface treated with adsorbent molecules, e.g. heparin, and which is therefore capable of binding the desired cancer mediators to remove them from the blood. It is also possible to use a microporous substrate in the present invention if surface treatment renders that substrate effectively nonporous.

This can occur intentionally or inadvertently, when surface treatments during media manufacturing block the pores.

This converts the microporous substrate to one that does not require diffusion of adsorbate into pores to bind to the media.

The claimed methods are intended to be applied in primarily in extracorporeal therapies or procedures, although implantable devices are also possible "Extracorporeal therapies" means procedures that are conducted outside the body, such as therapies in which desired products like oxygen, blood-anticoagulants, anesthetics etc can be added to body fluids. Conversely, undesired products like naturally occurring toxins or poisons can be also removed from body fluids with specific types of extracorporeal circuits. Examples are haemodialysis and haemofiltration which represent technologies whereby blood is depleted of waste products. Adsorption on activated carbon has been used to remove blood-borne poisons, and so forth.

Whole blood and blood serum from mammals can be used in the present invention. The amount of blood or blood serum that can be used in the claimed methods is not intended to be limited. It can range from less than 1 mL to above 1 L, up to and including the entire blood volume of the patient when continuous recirculation back to the patient is employed. One or more 'passes' through the adsorption bed may be used if needed. The blood may be human or animal blood.

Surface heparinized adsorption media to remove cancer mediators from blood are optimized according to the present invention for use in traditional extracorporeal blood circulation with flow rates >50 mL/min, and preferably between about 150 and 2000 mL/min. If measured by linear flow velocity, ≥8 cm/min, preferably about ≥24 cm/min and more preferably about 24-329 cm/min. Such high flow rates create short residence times within the adsorption column and convection transport dominates over Brownian diffusive transport. This is particularly important for binding large MW proteins or cytokines such as TNF-α and larger particles such circulating tumor cells, because they diffuse very, very slowly. In the present invention the dominant adsorption sites available for removing cancer mediators lie at the surfaces within the interstices of the media bed through which the blood flows or is delivered by forced convection. To treat blood, the interstitial channels need to be large enough to allow the transport of red blood cells, which are an average 6 microns in diameter. To allow a packed adsorption cartridge to be placed into an extracorporeal circuit with high blood flow rate, the interstitial channels must be several times larger than the diameter of red blood cells. This can prevent high shear rates that lead to hemolysis while simultaneously minimizing pressure drop in the blood that flows through the packed bed or cartridge. Additionally, the media is preferably rigid to minimize deformation that could clog the filter cartridge by compaction. Based on these preferences, an optimized rigid media balances interstitial channel size and total surface area, e.g., for efficient removal of cancer mediators in high-flow extracorporeal blood circuits.

2. The substrate used in the invention.

Various materials, in shape and composition, can be used as a substrate in the present invention. All suitable substrates provide high surface area while promoting the conveyance of adsorbates to the adsorbent sites that bind them (primarily) by forced convective transport. The media is typically provided packed within a container, such as a column, that is designed to hold the media so that it will not be carried away in the flowing blood (a.k.a. media migration) and permit the flow of blood past essentially all of the media's surface. Useful substrates for creating the adsorption media include non-porous rigid beads, particles, or packing, reticulated foams, a rigid monolithic bed (e.g. formed from sintered beads or particles), a column packed with woven or non woven fabric, a column packed with a yarn or solid or hollow dense (not microporous) monofilament fibers, a spiral wound cartridge formed from flat film or dense membrane, or a combination of media such as a mixed bead/fabric cartridge. A suitable substrate for use in the present invention is one that is initially microporous but becomes essentially nonporous when the surface is treated before, during or after the creation of adsorption sites, e.g., via end-point-attached heparin.

The column has a macroporous structure that presents a high surface area to the blood or serum while preventing a large pressure drop and high shear rates. In addition to the potential for damaging the blood by hemolysis, high pressure drops should be avoided because they can shut down extracorporeal circuits equipped with automatic shut offs that respond to pressure drop.

The substrate may also take the form of a dense a.k.a. barrier membrane. In this example, the surface of a non-porous film is modified by binding heparin and/or heparan sulphate together with optional adsorbing groups not derived from heparin or heparan sulphate to the membrane's surface. Alternatively, a microporous membrane may be rendered nonporous or 'dense' before, during or after attachment of binding sites by filling the pores with essentially non-porous material, e.g., a polymer. The membrane in sheet or (hollow) fiber form may be be arranged within a housing to present high surface area for blood contact that is suitable for use in the practice of the present invention.

2.1. Beads as Substrate

One useful substrate is in the form of solid beads or particles. The 'beads' can be made of materials that are sufficiently rigid to resist deformation/compaction under the encountered flow rates. Resistance to deformation is necessary to maintain the free volume and subsequent low pressure drop of the packed bed 'contactor'. The substantial lack of accessible pores in the bulk of the substrate eliminates the need for adsorbates to diffuse into the pores prior to adsorption. The adsorption sites of the present invention are primarily on the surface of the media and are thus positioned to be accessible to adsorbates in the blood delivered to that surface largely by convective transport. Suitable substrates need not be perfectly smooth on their surface since roughness produces a desirable increase in surface area for attachment of binding sites, e.g. by covalent or ionic bonding of heparin. Accessible internal pores with molecular dimension, on the other hand, are largely avoided to eliminate the need for adsorbates to diffuse into the pores before attaching to binding sites.

Various kinds of beads can be used in the invention. Useful beads should have sufficient size and rigidity to avoid deformation/compaction during use in the method, and have sufficient surface area to be capable of being coated with heparin for use in the method.

Evidence of sufficient substrate rigidity is the absence of a significant increase in pressure drop across the adsorption bed during about one hour of flow of water or saline at rates typical of clinical use: for example, <10-50% increase relative to the initial pressure drop (measured within the first minute of flow) when measured at similar flow rate, e.g., of saline.

The beads or other high-surface-area substrates may be made from a number of different biocompatible materials, such as natural or synthetic polymers or non-polymeric material including glasses, ceramics and metals, that are essentially free of leachable impurities. Some exemplary polymers including polyurethane, polymethylmethacrylate, polyethylene or co-polymers of ethylene and other monomers, polyethylene imine, polypropylene, and polyisobutylene. Examples of useful substrates include nonporous Ultra High Molecular Weight PolyEthylene (UHMWPE). Other suitable beads are polystyrene, high density and low density polyethylene, silica, polyurethane, and chitosan.

Methods for making such beads are per se known in the art. Polyethylene beads and other polyolefin beads are produced directly during the synthesis process and can often be used without further size reduction. Other polymers may need to be ground or spray dried and classified, or otherwise processed to create beads of the desired size distribution and shape.

As noted above, for use in the method of the invention, the size of the channels or interstitial space between individual beads for extracorporeal blood filtration should be optimized to prevent a high-pressure drop between the inlet and outlet of the cartridge, to permit safe passage of the blood cells between the individual beads in a high flow environment, and to provide appropriate interstitial surface area for binding of the heparin to the cancer mediators in the blood. In a close packed bed of 300-micron, roughly spherical beads, an appropriate interstitial pore size is approximately 68 microns in diameter. Useful beads have a size ranging from about 100 to above 500 microns in diameter. The average size of the beads can be from 150 to 450 microns. For example, polyethylene beads from Polymer Technology Group (Berkeley, USA) having an average diameter of 0.3 mm are suitable. The interstitial pore is a function of bead size.

For use, the suitable beads are housed in a container, such as a column. Other suitable forms of substrate are described below.

Reticulated foams have open cells and can be made from, for example, polyurethanes and polyethylenes. Control of pore size can be achieved by controlling the manufacturing method. In general, reticulated foams can have between 3 and 100 pores/inch and can exhibit a surface area of $\geq 66$ $cm^2/cm^3$.

Beads can be sintered into a monolithic porous structure through either chemical or physical means. Polyethylene beads can be sintered by heating the beads above their melting temperature in a cartridge and applying pressure. The resulting interstitial pore size is slightly reduced from the interstitial pore size of a packed bed of non-sintered beads of equal size. This reduction can be determined empirically and used to produce the desired final interstitial pore size.

A column or other housing shape can be packed with either woven or non-woven heparinized fabric or the heparin, heparan sulphate or optional non-heparin adsorption sites may be attached, e.g. by covalent, ionic or other chemical or physical bonds, after the housing has been filled with the substrate media. By controlling the fiber denier and density of the fabric during weaving or knitting or during the creation of a non-woven web, the interstitial pore size can be controlled. Useful non-woven fabrics may be in the form of felts, melt-blown, or electrostatically spun webs, having a random orientation held together by entanglement of the fibers and/or adhesion or cohesion of intersecting fibers. Useful woven fabrics have a more defined and non-random structure.

A column can be packed with fibers or yarns made from fibers. Polyethylene, and other fibers, can be drawn into thin hollow or solid monofilament fibers or multifilament yarns, that can be packed into cartridges in the same way that hollow fiber membranes are installed within conventional hemodialysis cartridges or blood oxygenators. In the present invention originally porous hollow fibers are rendered dense or non-porous before, during or after binding heparin or other adsorbents to the outer and/or inner surfaces. Dyneema Purity® from Royal DSM is a high-strength solid fiber made of UHMWPE. Dyneema can be heparinized and packed into a cartridge to provide a high-surface area support for the removal of cancer mediators.

A spiral wound cartridge contains a thin film or membrane that is tightly wound together with optional spacer materials to prevent contact of adjacent surfaces. The membrane can be made from polymers such as polyurethane, polyethylene polypropylene, polysulfone, polycarbonate, PET, PBT, etc.

2.1. Attachment of Heparin

The adsorption media of the present invention preferably comprises heparin covalently linked to the surface of the solid substrate. Various per se known methods can be used to attach heparin to the desired substrate, such as described in a review article by Wendel and Ziemer. (H. P Wendel and G. Ziemer, European Journal of Cardio-thoracic Surgery 16 (1999) 342-350). In one embodiment, the heparin is linked to the solid substrate by covalent end-point attachment. This method increases the safety of the device by reducing or eliminating the release of heparin from the substrate surface that could enter the blood stream. 'Leaching' of heparin by and into the blood is to be avoided because it can increase the risk of bleeding and heparin-induced thrombocytopenia.

Covalent attachment of heparin to a solid substrate provides better control of parameters such as surface density and orientation of the immobilized molecules as compared to non-covalent attachment. The surface concentration of heparin on the solid substrate can be in the range of 1-10 $\mu g/cm^2$. Covalent end-point attachment means that heparin is covalently attached to the solid substrate via the terminal residue of the heparin molecule. Heparin can also be bound at multiple points. The end-point attachment is preferred.

If beads are used, it is preferred that they be hydrophilized prior to attachment of the heparin or other compound. Possible methods of preparing the beads include acid etching, plasma treating, and exposure to strong oxidizers such as potassium permanganate.

Amount of Heparin/Gram Substrate

The amount of heparin per gram substrate can vary. If beads are used, the amount of heparin per gram bead is determined by the number of layers used and also the size of the beads. The larger the bead, the less heparin per gram of bead is achieved. One preferred amount is 2.0±0.5 mg heparin/g bead per the MBTH method.

The molecular weight of heparin used in the claimed methods can vary. For example, native heparin has an average molecular weight of 22 kDa. Nitric acid degraded heparin has a molecular weight of 8 kDa.

3. Device for Use in the Methods of the Invention

Another aspect of the present invention provides use of a device comprising the heparin modified solid substrate, the heparin having a binding affinity for cancer mediators, for extracorporeal removal of the cancer mediators from mammalian blood.

A device as referred to in the use and method according to the invention may comprise a conventional device for extracorporeal treatment of blood and serum from patients, e.g. suffering from renal failure.

Local blood flow patterns in blood contacting medical devices for extracorporeal circulation are known to influence clot formation via shear activation and aggregation of platelets in stagnant zones. Consequently, a device as used in the various aspects of the invention should be designed in a fashion that does not create these problems.

A device as used in some embodiments of the invention may for example have the following properties:

A blood flow in the range of 150-2000 ml/min, or if measured by linear flow velocity of ≥8 cm/min.
Low flow resistance.
Large surface area of substrate having carbohydrates immobilized thereto, e.g. about 0.1-1 m².
Stable coating (no clinically significant leakage of carbohydrate to the blood in contact therewith).
Proper haemodynamic properties in the device (no stagnant zones).
Optimal biocompatibility.

A non-limiting example of such a device, which can be used in a use or a method according to the present invention, is a pediatric haemoflow dialyzer such as the extracorporeal blood filtration device for removing cytokine molecules to be compatible with high flow rates from Exthera Medical. Other models or types of devices for extracorporeal treatment of blood or serum may also be used, such as the Prisma M10 haemofilter/dialyzer from Gambro AB, Sweden.

High-flow conditions can be defined as blood flow above the diffusion limit.

4. Combining the Inventions with Additional Filtration/Separation Steps

In an embodiment of the treatment method according to the present invention, the extraction and reintroduction of blood may be performed in a continuous loop, which loop comprises a part of the bloodstream of the subject.

In a further aspect the methods described above can be combined with other methods to filter or treat mammalian blood. For example, a cartridge that is based on convection kinetics can then be used in series with conventional extracorporeal circuits such as CPB, hemodialysis, and oxygenation.

5. Examples

The various aspects of the invention are further described in the following examples. These examples are not intended to be limiting.

Example 1

Preparation of Heparin Column

Polyethylene (PE) beads, with an average diameter of 0.3 mm (lot no. 180153), are supplied by the Polymer Technology Group (Berkeley, USA) and the columns (Mobicol, 1 mL) are obtained from MoBiTec (Germany). Heparin and polyethyleneimine (PEI) are purchased from Scientific Protein Laboratories (Waunakee, Wis., USA) and BASF (Ludwigshafen, Germany) respectively. All chemicals used are of analytical grade or better.

Immobilization of heparin onto the beads was performed as described by Larm et al. (Larm O, Larsson R, Olsson P. A new non-thrombogenic surface prepared by selective covalent binding of heparin via a modified reducing terminal residue. *Biomater Med Devices Artif Organs* 1983; 11: 161-173).

The polymeric surface was heparinized using the general procedure described below.

The polymeric surface is etched with a oxidizing agent (potassium permanganate, ammoniumperoxidisulfate) in order to introduce hydrophilic characteristics together with some reactive functional groups (—$SO_3H$, —OH, —C=O, —C=C—). The surface can also be etched with plasma or corona. For example, the PE-beads are etched with an oxidizing agent (potassium permanganate in sulphuric acid).

These hydrophilized beads, inter alia containing OH-groups and double bonds, are later used as controls.

Reactive amino functions are introduced by treatment with a polyamine, polyethylenimine (PEI) or chitosan. For some purposes the polyamines may be stabilized on the surface by cross linking with bifunctional reagents, such as crotonaldehyde or glutaraldehyde.

The coating is further stabilized by ionic cross linking with a sulfated polysaccharide (dextran sulfate or heparin). If necessary these steps are repeated and a sandwich structure is built up. Careful rinsing (water, suitable buffers) should be performed between each step. After a last addition of PEI or chitosan, end-point attachment (EPA) to the aminated surface of native heparin is done by reductive amination, utilizing the aldehyde function in the reducing terminal residue in native heparin.

A more reactive aldehyde function in the reducing terminal residue can be achieved by partial, nitrous degradation of heparin. This shortens the reaction time, but the immobilized heparin will have a lower molecular weight. The coupling is performed in aqueous solution, by reductive amination (cyanoborohydride, $CNBH_3^-$).

In this alternate method, the aminated media is suspended in acetate buffer (800 ml, 0.1 M, pH 4.0) and 4.0 g nitrous acid degraded heparin (heparin from Pharmacia, Sweden) was added. After shaking for 0.5 h, $NaBH_3CN$ (0.4 g) was added. The reaction mixture was shaken for 24 h and then processed as above, yielding heparinized media.

1-10 μg/cm² of heparin can be coupled to all hydrophilic surfaces like glass, cellulose, chitin etc, and more or less all hydrophobic polymers like polyvinyl chloride, polyethylene, polycarbonate, polystyrene, PTFE etc.

The resulting PE-beads, with covalently end-point attached heparin, are sterilized with ethylenoxide (ETO) and rinsed with 0.9% sodium chloride and ultra pure water. The amount heparin was determined to be 2.0 mg heparin/g bead with the MBTH method. (Larm O, Larsson R, Olsson P. A new non-thrombogenic surface prepared by selective covalent binding of heparin via a modified reducing terminal residue. Biomater Med Devices Artif Organs 1983; 11: 161-173 and Riesenfeld J, Roden L. Quantitative analysis of N-sulfated, N-acetylated, and unsubstituted glucosamine amino groups in heparin and related polysaccharides. Anal Biochem 1990; 188: 383-389).

The polyethylene beads had a mean diameter of 0.3 mm and are heparinized with a technology that guaranteed that the heparin molecules are covalently end point attached to the surface, thereby making the carbohydrate chains more accessible for proteins with affinity for heparin/heparan sulphate. The mean molecular weight of the immobilized heparin was about 8 kDa, while 2 mg (equal to approximately 360 IU) was coupled to each gram of beads. The integrity of this surface was verified by the expected removal of 75% of antithrombin (AT) concentrations from the blood passed over heparinized, but not non-heparinized, beads.

These data corresponds well with the previous observations from extracorporeal lung assistance (ECLA) on septic patients using surface heparinized oxygenators published by Bindslev et al. (Bindslev L, Eklund J, Norlander O, Swedenborg J, et al. Treatment of acute respiratory failure by extracorporeal carbon dioxide elimination performed with a surface heparinized artificial lung. *Anesthesiology* 1987; 67: 117-120.)

Mixture of Beads with Different Surface Functionality

Heparin is well known to be a biologically active carbohydrate that can bind cytokines, pathogens, and many other proteins. In addition, heparin has the advantage of being safe as it is also a well-known anticoagulant. Manufacturers have coated medical devices with heparin for years to improve their safety. Therefore, the heparinized surface in the adsorption cartridges described here provides both the safety and efficacy of the device for removing harmful substances from blood or other biological fluids.

In addition to heparin and heparin sulfate, there are other biologically active carbohydrates that can remove different types of harmful substances from blood and biological fluids. Other carbohydrates of interest include sialyic acic, heparan sulfate, chondroitin sulfate, dermatan sulfate, and hyaluronic acid. However, these carbohydrate surfaces may be significantly less blood compatible than heparinized surfaces and can lead to increased thrombogenicity. A cartridge containing these additional carbohydrate surfaces as the bioactive adsorbant could be assembled to remove different cancer mediators from blood, however, due to the clotting risk of the device, the patient would need a high dose of systemic anticoagulation which could lead to a bleeding risk.

By assembling an adsorption cartridge with both heparinized surfaces and additional carbohydrate chemistry, many different cancer mediators can all be removed from blood or biological fluid while maintaining the safety of the device.

Use of heparinized cartridge during tumor excision surgery.

When a tumor is excised, there is a high potential of release of metastatic cancer cells into the blood stream that can then spread the cancer to additional parts of the body. A heparinized cartridge is used to remove circulating cancer cells during and after the surgical procedure. The flow rate of blood through the circuit is maintained at 150 ml/min. After the surgery is complete, the cartridge continues to cleanse the blood for 2- or more hours to remove circulating tumor cells.

Use of Heparinized Cartridge to Circulating Tumor Cells

In combination with an assay that detects circulating tumor cells in cancer patients, a heparinized cartridge is used to selectively remove the circulating tumor. The filtration is initiated when either a biosensor or bioassay, sensitive to tumor cells, detect the presence of tumor cells in blood. An example of an FDA approved circulating tumor cell detection technology is the CellSearch® Circulating Tumor Cell (CTC) Test from Veridex.

Use of Heparinized Cartridge to Remove Circulating Heparanases

Heparanases are also implicated in cancer metastases by degrading HS segments on the ECM which then compromises endothelial cells for tumor cell invasion. A heparinized cartridge is used to selectively remove heparanases to protect the ECM. The filtration is initiated when either a biosensor or bioassay, sensitive to heparanase, detects the presence of heparanase.

Use of Heparinized Cartridge to Remove Circulating Growth Factors

Growth factors such as (VEGF) and basic fibroblast growth factor (bFGF) are implicated in cancer angiogenesis. A heparinized cartridge is used to selectively remove growth factors to prevent angiogenesis. The filtration is initiated when either a biosensor or bioassay, sensitive to growth factors, detect the presence of growth factors.

Use of Heparinized Cartridge in Combination with Radiation and Chemotherapy

The heparinized adsorption cartridge can bind cancer mediators circulating in blood, however it cannot treat the tumor or cancerous cells not circulating in blood. The heparinized cartridge can be used in combination with traditional cancer therapy such as radiation and chemotherapy. The radiation or chemotherapy can treat the non circulating tumors and cancer cells while the heparinized cartridge removes circulating cancer mediators.

Other Examples

A device according to the present invention can also take other forms, depending upon the specific environment for use of the device:

1) Wearable and portable integrated devices, such as:
   a. Low pressure drop optimized heparinized cartridge pumped by arterial pressure.
   b. Wearable for prolonged duration when risk of metastases is high.
   c. Simple cartridge exchange system for home use
   d. Sensors to close valves in case of clot formation
   e. On-board diagnostics The method according to the invention permits access to blood from vasculature e.g., before, during and/or after tumor surger, thereby allowing for immediate capture of mediators released from a tumor site.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

The invention claimed is:

1. A method for treating cancer progression or cancer metastasis by removing circulating cancer cells from mammalian blood, the method comprising: contacting mammalian blood with a solid substrate coated with end-point attached heparin, which end-point attached heparin has a binding affinity for the circulating cancer cells, wherein circulating cancer cells are bound to end-point attached heparin coated on the solid substrate to thereby remove circulating cancer cells from mammalian blood and thereby treat cancer or cancer metastasis.

2. A method for treating cancer, the method comprising: removing circulating cancer cells from blood of a mammal that has undergone surgery, wherein the circulating cancer cells have been generated by the surgery, by contacting the mammalian blood with a solid substrate coated with end-point attached heparin, wherein the circulating cancerous cells are bound to end-point attached heparin coated on the solid substrate, and returning the blood to the mammal to treat cancer.

3. The method according to any one of claims 1-2, wherein said contacting blood from a patient is conducted during and/or after surgery to remove a tumor.

4. The method of claim 1 or 2, wherein said solid substrate comprises a packed column of non-porous rigid beads or particles, a column packed with a rigid reticulated foam, a column packed with a rigid monolithic bed of sintered beads or other sintered solid media with internal flow channels, a column packed with woven or non-woven rigid fabric, a column packed with a rigid yarn or optionally hollow monofilament fibers, a spiral wound cartridge, or a combination of at least two members selected from the group consisting of beads, rigid reticulated foam, sintered beads, fabric, yarn and monofilament.

5. The method according to claim 4, wherein the solid substrate comprises polyethylene beads.

6. The method according to claim 1 or 2, further comprising at least one additional polysaccharide coated on the solid substrate selected from the group consisting of heparan sulphate, hyaluronic acid, sialic acid, carbohydrates with mannose sequences, and chitosan.

\* \* \* \* \*